United States Patent [19]

Lesniak

[11] Patent Number: 5,582,485
[45] Date of Patent: Dec. 10, 1996

[54] STRUCTURE ANALYSIS METHOD USING TIME-VARYING THERMAL SIGNAL

[75] Inventor: Jon R. Lesniak, Madison, Wis.

[73] Assignee: Stress Photonics, Inc., Madison, Wis.

[21] Appl. No.: 351,817

[22] Filed: Dec. 8, 1994

Related U.S. Application Data

[62] Division of Ser. No. 122,892, Sep. 15, 1993, Pat. No. 5,376,793.

[51] Int. Cl.$^6$ .................................................. G01N 25/72
[52] U.S. Cl. .............................................. 374/5; 374/124
[58] Field of Search ............................... 374/4, 5, 6, 7, 374/124; 250/330, 332, 341.8

[56] References Cited

U.S. PATENT DOCUMENTS

| | | | |
|---|---|---|---|
| 4,172,382 | 10/1979 | Murphy et al. | 73/40.5 A |
| 4,184,768 | 1/1980 | Murphy et al. | 356/326 |
| 4,468,136 | 8/1984 | Murphy et al. | 374/45 |
| 4,513,384 | 4/1985 | Rosencwaig | 374/7 |
| 4,589,783 | 5/1986 | Thomas et al. | 374/45 |
| 4,724,482 | 2/1988 | Duvent | 358/113 |
| 4,798,477 | 1/1989 | Mountain | 374/45 |
| 4,854,724 | 8/1989 | Adams et al. | 374/5 |
| 4,866,276 | 9/1989 | Leavens et al. | 250/341 |
| 4,874,251 | 10/1989 | Thomas et al. | 374/45 |
| 4,878,116 | 10/1989 | Thomas et al. | 358/160 |
| 4,886,370 | 12/1989 | Koshihara et al. | 374/5 |
| 4,968,144 | 11/1990 | Thomas et al. | 356/354 |
| 4,983,836 | 1/1991 | Matoba et al. | 250/330 |
| 5,012,112 | 4/1991 | Flint et al. | 250/493.1 |
| 5,111,048 | 5/1992 | Devitt et al. | 250/342 |
| 5,118,945 | 6/1992 | Winschuh et al. | 250/341 |
| 5,201,582 | 4/1993 | Lesniak | 374/45 |
| 5,208,766 | 5/1993 | Chang et al. | 364/552 |
| 5,292,195 | 3/1994 | Crisman, Jr. | 374/4 |
| 5,399,016 | 3/1995 | Martin | 374/7 |

FOREIGN PATENT DOCUMENTS

| | | | |
|---|---|---|---|
| 1485110 | 6/1989 | U.S.S.R. | 374/5 |

OTHER PUBLICATIONS

Cramer, et al. "Thermographic Imaging of Cracks in Thin Metal sheets," 162/SPIE vol. 1682 *Thermosense XIV.* 0–8194–0843–Mar., 1992.

Favro et al., "Inversion of pulsed thermal–wave images for defect sizing and shape recovery," 178/SPIE vol. 1682 *Thermosense XIV.* 0–8194–0843–Mar., 1992.

Spicer et al., "Source patterning in time–resolved infrared radiometry (TRIR) of composite structures," 248/SPIE vol. 1682 Thermosense XIV. 0–8194–0843–Mar., 1992.

*Primary Examiner*—Diego F. F. Gutierrez
*Attorney, Agent, or Firm*—Lathrop & Clark

[57] ABSTRACT

An instrument employs a projector which projects a moving pattern of heat onto a test object. An exemplary pattern is formed of bars or lines of infrared radiation separated by unheated areas, or areas of shadow. An infrared camera which is not sensitive to the wavelength of the projected light is used to detect the heat emitted by the test object. The projected bands of thermal radiation heat the surface of the test object. Some of the energy in the form of heat sinks into the structure, while some of the heat energy flows laterally from the heated band to the unheated bands between the projected bands. The lateral flow of heat between bands is resisted by cracks in the surface. This resistance causes heat energy to build up on one side of each crack. The downward flow of heat energy is resisted by less conductive material such as a debonding between layers which traps the heat, causing it to build up laterally. Thus, flaws caused by cracks normal to the surface and delaminations or cracks parallel to the surface may be detected by the same device.

4 Claims, 6 Drawing Sheets

($\int$cc+$\int$sc)

($\int$cs+$\int$ss)

Temporal Sine & Cosine Components

FIG. 7

$|\emptyset(x,t)|$

Amplitude

STRUCTURE ANALYSIS METHOD USING TIME-VARYING THERMAL SIGNAL

This is a division of application Ser. No. 08/122,892, filed Sep. 15, 1993, now U.S. Pat. No. 5,376,793.

FIELD OF THE INVENTION

This invention relates to methods and apparatus for the thermal imaging of objects in general and methods employing the thermal diffusivity of the object in particular.

BACKGROUND OF THE INVENTION

Engineering science and design methods are generally based on the assumption that engineering materials are homogeneous, or in the case of composites, have properties which vary with the orientation of the material in a known and uniform manner. A second useful and widely applied assumption is that engineering materials are sufficiently ductile that small local inhomogeneities can be ignored. However, in many real world structures, particularly those which are highly engineered to meet demanding design criteria or which employ advanced materials, local inhomogeneities, such as cracks and de-laminations, determine the large-scale structural performance.

Another type of highly-engineered structure in which it is necessary to determine local material properties is typified by turbine blades for use in the hot section of modem jet engines, which are among the most highly engineered of modem structures. Such parts must withstand high stresses and high temperatures in an abrasive and chemically hostile environment.

To meet these design demands, blades grown of single crystals of metal are given multiple coatings, for example, to resist heating, abrasion, and corrosion. The reliability of these blades is dependant on the ability to detect any flaw in a bonding between the various layers and the underlying metal of the blade. Many methods have been devised and put to use. X-ray examination has been found useful for detecting in-depth density variations; yet x-ray examination requires access to both sides of a specimen. Further, x-rays can involve the use of hazardous materials, and are not always successful in detecting cracks or de-laminations which do not produce density variations.

Dye-penetrant, ultrasound, and eddy-currents have been used to detect weld flaws, de-lamination in structural composites, and other undesirable structure attributes. These methods, however, can be labor intensive, require physical contact with the test object, and often require special preparation of the material's surface.

A belief that thermal imaging (thermography) would lead to more cost-effective material flaw detection has led to a number of techniques employing thermal radiation and the test specimen's reaction to the thermal radiation to detect material flaws.

One such technique employs a high-power, pulsed thermal wave, which propagates into the material as a planar wave of thermal energy. When the thermal wave reaches a defect within the depth of the object being tested, that portion of the wave which encounters the defect is reflected with the amount of the reflected energy dependant on the nature of the discontinuity. The reflected wave is detectable at the surface by thermal imaging. This method, while being useful in some circumstances, requires high-power flash lamps and does not detect flaws which are normal to the surface of the object being tested.

Another thermal imaging process for detecting material defects, particularly stress cracks, employs a laser which performs a raster scan of a test object while the test object is being thermally imaged. This method requires a laser of relatively high power and detects surface cracks by their greater absorption of energy. This method can be somewhat sensitive to the angle of incidence. Further, the decay of the transient thermal response of the crack must be carefully analyzed to distinguish surface blemishes from cracks having significant depth. This method also requires a relatively clean surface, free of surface film and paint.

Another known technique, sometimes referred to as the "mirage effect," employs a heating laser which generates an output which is intensity modulated to provide a periodic optical signal used to periodically heat a point on the surface of an object. The optical beam from a probe laser passes parallel to the surface of the object through the heated zone. This probe beam is deflected from a normal path due to density variations in the air above the surface of the sample caused by the heating of the surface by the probe laser. The deflection of the probe laser from its nominal path indicates the presence of surface or sub-surface cracks, flaws or voids in the object being tested. This type of apparatus requires a scan head located relatively close to the surface of the object being tested to recover the output of the probe beam.

One method for detecting flaws in welds involves heating the weld with an infrared source and observing the heated weld with an infrared camera to detect the thermal response of the weld, which may be indicative of weld flaws.

In principle, thermographic testing involves exposure of the analyzed surface to even heating. Variations in the thermoconductivity of the features below the surface then allow heat to flow away from the surface more rapidly in some places than other, establishing temperature gradients along the surface that provide an indication of the sub-surface features in an object.

One type of apparatus which employs the thermographic technique has a linear heat source which is passed in spaced relation over the surface in front of a row of detectors. The heat source establishes a temperature gradient on the surface being tested. The sensors monitor the temperature gradient for variations which indicate surface defects. This process suffers from requiting the heat source and the detector to be moved closely over the surface of the object to be tested.

One variation on this process of using lateral heat flow to detect sub-surface flaws involves using a linear heating source, such as a laser projected through a cylindrical lens and an infrared scanner which views a line of material spaced from, and off-set from, the linear heat source. Variations in the temperature gradient between the heat source and the infrared scanned line indicate the presence of cracks and material defects in the tested sample. This system is experimental in nature and requires a relatively intense heat source, with a change of temperature gradients in the material which can amount to several degrees or more.

What is needed is an apparatus which is able to detect sub-surface cracks and flaws and which can image entire test objects from a distance while utilizing low levels of thermal stimulation.

SUMMARY OF THE INVENTION

The forced diffusion thermographic instrument of this invention employs a projector which projects a moving pattern of heat onto a test object. For example, a pattern formed of moving lines of thermal radiation may be projected onto a test object. If the test object is a flat plate the projector will project narrow bars or lines of radiation which will sweep across the specimen. The bars or lines of infrared radiation are separated by unheated areas, or areas of shadow. An infrared camera which is not sensitive to the wave-length of the projected light is used to view the test object. The projected bands of thermal radiation heat the surface of the test object. Some of the energy in the form of heat sinks into the structure, while some of the heat energy flows laterally from the heated band to the unheated bands between the projected bands. The lateral flow of heat between bands is resisted by any cracks in the surface which cause heat energy to build up on one side of each crack. The downward flow of heat energy is resisted by less conductive material such as a debonding between layers which traps the heat, causing it to build up at the surface. Thus, flaws caused by cracks normal to the surface and de-laminations or cracks parallel to the surface may be detected by the same device.

Continuous dynamic pattern projection produces three distinct benefits. First, and perhaps most critically, the moving pattern produces a periodicity to the thermoradiations from the test object. This allows auto-correlation, or a lock-in amplifier, to be employed on the output of the camera. Because the signal of interest is periodic with time, it is possible, using a digital or analog lock-in amplifier, to distinguish the thermal response of the material due to the projected moving pattern, and not due to random thermal noise, temperature-gradient aspect ratio, etc. In this way temperature differentials as small as 0.001° K. will be detected. This in turn means that a relatively low-power projector may be used to illuminate a large test object.

The second advantage gained by moving a thermal pattern is the reduction of areas without heat flow. Where linear bars are used, the only direction in which heat is not flowing is that parallel to the orientation of the bars. Thus, cracks which are transverse to the parallel bars will not be detected. However, the simple process of analyzing the structure with projected bars of first one orientation superimposed on bars of a second orientation normal to the first, or the use of three sets of bars at 60° to each other, will ensure that heat flows occur across cracks so as to make them visible.

The third benefit derived from utilizing a moving pattern is that the spatial and temporal frequencies of the heating pattern may be controlled. For example, if projected heating bars are used, then the line density and the velocity of the movement of the bars over the test object can be used to differentiate between increased temperatures caused by cracks and those caused by disbonds or de-laminations. A crack prevents lateral heat flow on the surface of the object and to whatever depth the crack extends. In contrast, disbonds or delaminations between the layers within the depth of the material only affect the surface temperatures if the linear bars heat a particular location for a sufficient length of time. Therefore, by varying the frequency of spacing of the lines, surface phenomena such as cracks may be differentiated from disbonds or de-laminations. Further, by varying the frequency, the depth of the debond or de-lamination may be determined.

It is an object of the present invention to provide an instrument for detecting flaws in materials which uses the variations in diffusivity of an object to detect the presence of flaws.

It is another object of the present invention to provide an apparatus and method for flaw detection in a material which is capable of analyzing the entire field of view of the apparatus.

It is a further object of the present invention to employ an instrument and method for detecting flaws in a object which employs a time-varying thermal stimulation of the object, together with a time domain correlation of the thermal image of the same object.

It is a still further object of the present invention to provide an instrument and method for detecting flaws in an object which can differentiate between flaws which are normal to and flaws which are parallel to the surface of the object.

It is a still further object of the present invention to provide a test instrument and method which employs an adaptive projector, the projected pattern of which is adapted to the observed discontinuities in the object undergoing test.

It is yet another object of the present invention to provide a method and apparatus which employs varying frequencies of an illuminating pattern to examine the material in varying depth.

It is yet a further object of the present invention to provide a non-destructive test method which does not disrupt other activity being conducted around the test object.

Further objects, features and advantages of the invention will be apparent from the following detailed description when taken in conjunction with the accompanying drawings.

DESCRIPTION OF THE PREFERRED EMBODIMENT

Figure 1:
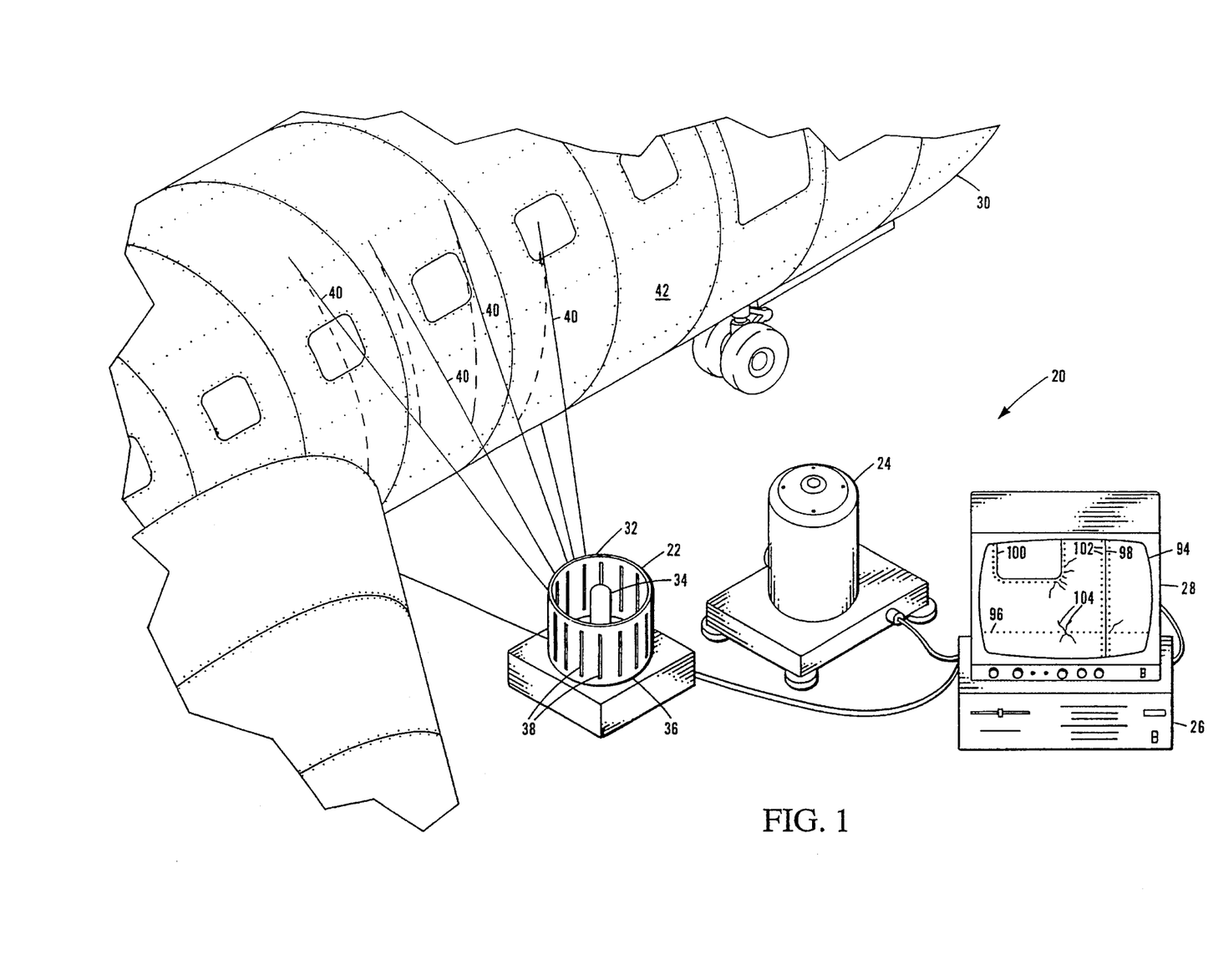
FIG. 1 is an isometric, pictorial view of the thermal imaging apparatus of this invention and an aircraft test specimen.

Referring more particularly to FIGS. 1–10, wherein like numbers refer to similar parts, FIG. 1 shows a forced diffusion thermography apparatus 20, which is composed of an infrared projector 22, an infrared camera 24, an imaging processor 26, and a display monitor 28. An object undergoing test 30, which is represented as an airplane in FIG. 1, is illuminated by the infrared projector 22, represented in FIG. 1 for simplicity as a rotatable mask or light shield 32, with a central infrared illumination source 34. The light shield 32 has a rotating cylinder 36, into which are cut parallel, equally spaced projection slots 38, which project bands 40 onto the surface 42 of the airplane 30. Because the cylinder 36 containing the projection slots 38 is rotating, the projected bands 40 sweep across the surface 42 of the airplane 30.

An infrared camera 24 focuses an image of the object being tested 30 onto a focal plane array (not shown) within the body of the camera. The camera is preferably of one of the type disclosed in my earlier U.S. Pat. No. 5,201,582, which is incorporated herein by reference. The camera normally incorporates an infrared filter (not shown) which rejects or absorbs the wavelengths shorter than one to three microns, thus preventing reflected light from the IR source 34 from reflecting off aircraft 30 surface 42 into the camera 24. A sensor array is located within the camera, and is for example, an exemplary system employing a high-performance 128×128 InSb focal plane array such as is available from Amber Engineering, Inc., 5756 Thornwood Drive, Santa Barbara, Calif., 53117-3802. In the exemplary 128×128 array, each sensor has a detector which is connected by an indium bump to a high-performance integrating amplifier which converts the detected signal to a band-limited voltage.

Each photo diode is connected to a capacitor, and as photons impact the surface of the photo diode, the capacitor is charged. Because the capacitor continues to charge as long as the photo diode receives photons, the capacitor acts as in integrator which integrates the output of the diode over the readout cycle of the array. Periodically, for example, 160 times a second, the value of the capacitors are sequentially read out. The readout of a diode may employ a local offset as disclosed in my earlier patent referred to above. A reference signal may be obtained by positioning a photodetector to detect the infrared pattern or in the case of a computer generated pattern the computer can provide the synchronous signal.

More critical, however, is the use of a digital correlator or lock-in amplifier on the output of each diode which correlates the signal each diode receives with the known periodicity of the thermal signal of interest. The use of a digital lock-in filter, explained more extensively in my prior patent, U.S. Pat. No. 5,201,582, may be thought of as simply a digital filter which filters out the portion of the output of the diode array which does not varies in time with the periodicity of the stimulating pattern 44, which is composed of individual projected bands 40, which move with a given frequency past a given point on the surface 42 of the test object 30.

One of the ways that the forced diffusion thermography apparatus 20 differs from prior attempts to make use of heat flow is that the lock-in amplification performed by the camera 24 allows the heat flows resulting from temperature differentials of a mere fraction of a degree to be readily imaged. The ability to image small temperature differentials makes the application of the thermographic apparatus 20 to large structures practical. The output of the IR projecting device 22 need only be from a fraction of a watt per square centimeter to about ten watts per square centimeter. The relatively low-power output required by the IR projector 22 means that whole sections of the test object 30 may be imaged at one time. The output of the synchronized IR camera 24 generates the thermal sine and cosine images 46 shown in FIG. 5. The thermal image 46 shows hot bands 48 and cool bands 50 as they would appear in the thermal image of the aluminum plate test specimen 60 shown in FIG. 2.

One way of conceptualizing how the lock-in amplification is used to produce the thermal image 46 is to consider the output of the IR camera to be converted by a Fourier transform into the frequency domain. The information which is correlated with the frequency of the IR pattern, for example 10 hertz, is selected from the frequency domain and transformed back to produce the thermal image 46.

Lock-in amplification is the process of using digital or analog circuits to implement a mathematical algorithm to extract information from a noisy signal, based on the information being correlated to some known parameter. In the application herein described the known parameter is the temporal frequency of the information of interest.

Figure 4:
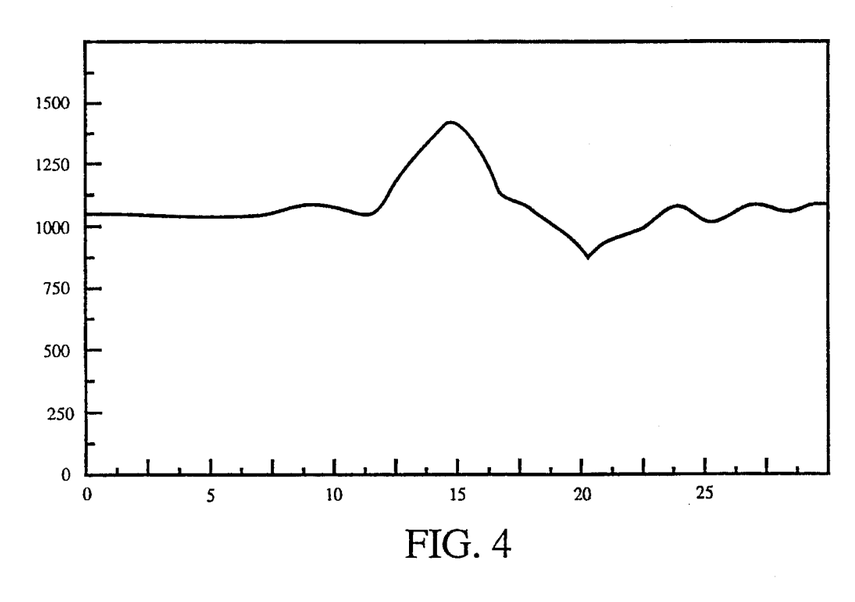
FIG. 4 is a graphical view of a thermal amplitude along line 4—4 in FIG. 2 which has been processed to reveal the temperature abnormality caused by the crack in FIG. 2.
Figure 6:
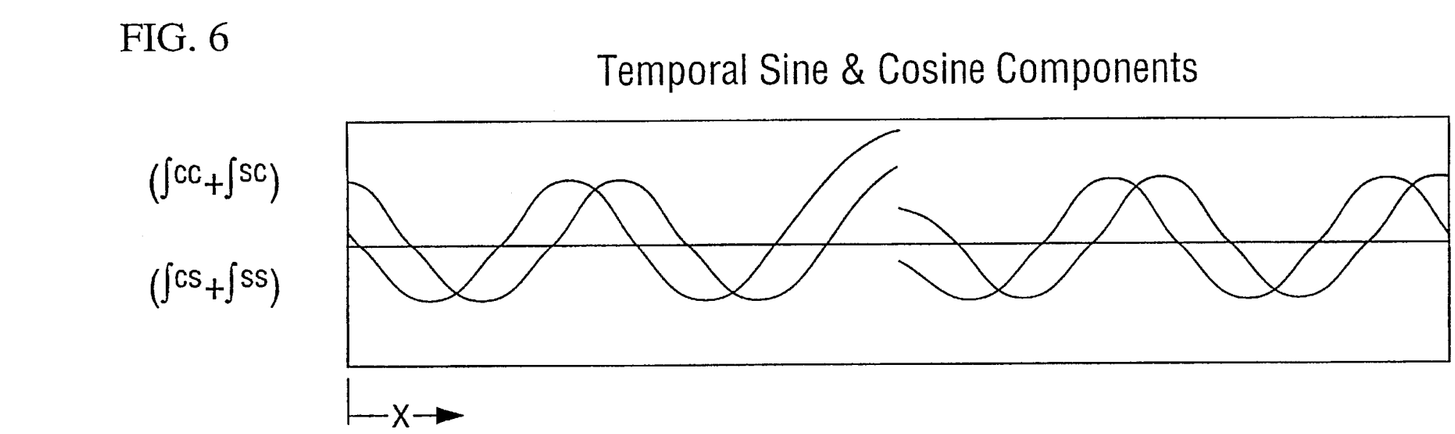
FIG. 6 is a graphical view of the temporal sine and cosine components of the thermal radiation produced by the apparatus of this invention along section line 3—3.
Figure 7:
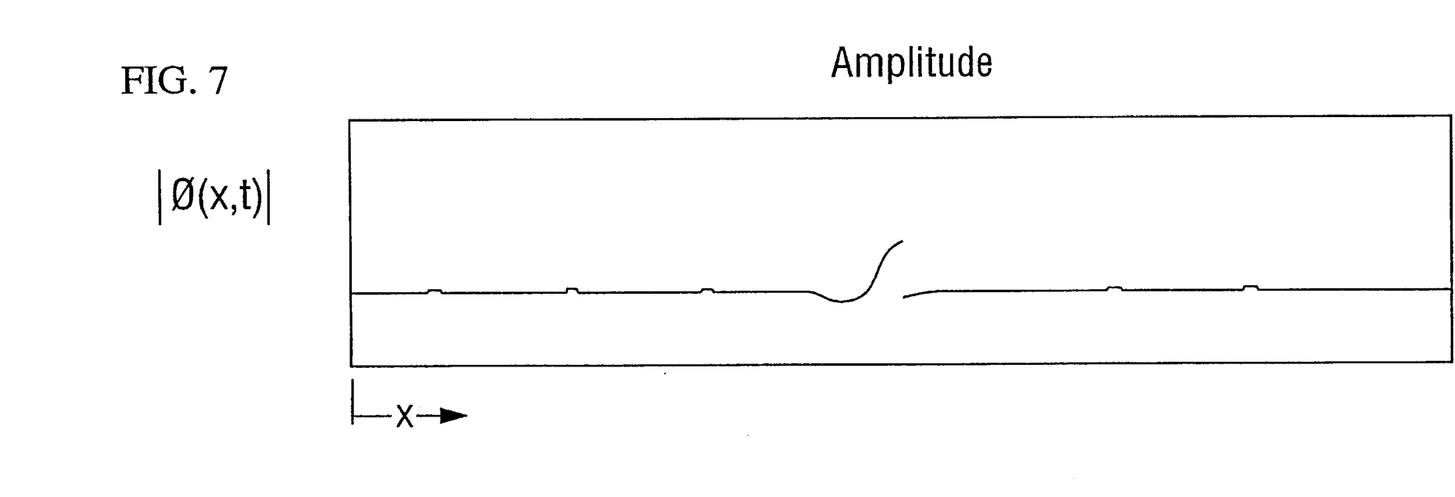
FIG. 7 is a graphical view of the thermal amplitude in the plate of FIG. 2 taken along section line 3—3.

In practice, employing the lock-in amplification technique disclosed in my earlier patent, temporal sine and cosine components are produced as illustrated in FIG. 6. The output of FIG. 6 has been produced by computer simulation of the test ease shown in FIG. 2, a 2" square aluminum plate 60 with a closed fatigue crack 54. The temporal sine and cosine components of the IR signal produced by the camera 24 are 90° out of phase. The sine and cosine components may be combined by a fast-image processing or spatial filter 56, which produces an amplitude variation illustrated in FIG. 7, which produces a flaw image 58. FIG. 4 shows actual test data of the amplitude taken along a test specimen 60 shown in FIG. 2.

The sine and cosine components may also be used to calculate the thermal diffusivity at each point in the image.

Where the surface 42 of test object 30 is uniform, such as in the test specimen 60 surface 62, the temperature profiles produced by the hot band 48 and cool band 50 will be uniform along the material. Thus, when the images correlated with the sine or cosine are properly combined, the net result is a constant. However, where a crack 54 produces a discontinuity causing an increase of temperature on the upstream side 64, and a cooling in the downstream side 66, a temperature profile such as shown in FIG. 4 or flaw image 58 is produced when the sine and cosine temporal component of the image are combined.

Referring to FIG. 3a–3e, beams of infrared radiation 68 are shown. For illustrative purposes one beam 68 is shown producing a hot band 48 on the surface 62 of the test specimen 60. In FIGS. 3a–3e, a cross-sectional surface 70 of the test specimen 60 is shown. The beams of infrared radiation 68 are shown moving from left to right by arrow 72 in FIGS. 3a–3e. Thus the movement of the beams 68 establishes an upstream side 64 and a downstream side 66 of the crack 54.

Three thermal contours of the temperature profile produced within the test specimen 60 by a beam 68 are also shown in FIGS. 3a–3e. A thermal contour is a line connecting points of equal temperature on a surface, with darker shading representing higher temperature in FIGS. 3a–3e. The first contour 74 surrounds a region 76 of higher temperature. The second contour 78 surrounds a region 80 of somewhat lower temperature. The third contour 82 encloses a region of still lower temperature 84.

Figure 3A:
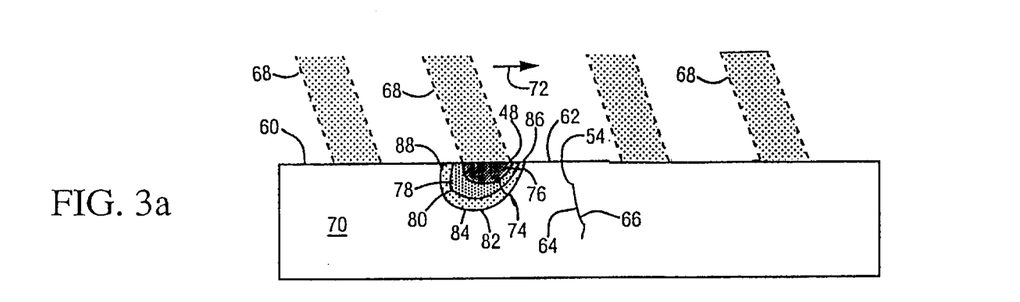
FIGS. 3a–3e are a series of sequential cross-sectional views illustrating the movement of a bars of infrared radiation along the plate of FIG. 2 taken along section line 3—3, where the heating caused by one bar is illustrated.

Because the heat source or beams 68 move from left to right, the temperature contours 74, 78, 82 are not evenly disposed about the hot band 48, but rather there is a small pre-heat zone 86 in front of the beam, and a larger post-heat zone 88 which lags the beam. The contours are pushed together where the beams are progressing into them in the leading pre-heat zone and are stretched out along the trailing post-heat zone 88. The IR camera images the surface 62 and therefore can see the contours 74, 78, 82 only where they reach the surface 62. FIG. 3a shows a heating beam of infrared radiation 68 and the contours 74, 78, 82 well away from the crack 54, and thus represents the nominal appearance of the temperature profile of the beam 68 as it moves along the test specimen 60.

The fatigue crack 54, even if it does not represent a physical separation of the upstream side 64 from the downstream side 66, does represent a break in the molecular bond between the material and thus there is less efficient transfer of heat from one side 64 to the other 66 of the crack 54. Thus the crack 54 represents a thermal barrier which restricts the flow of heat.

Figure 3B:
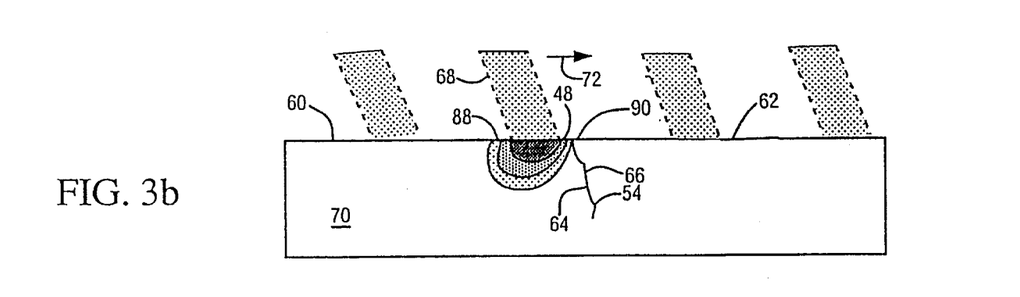
Figure 3C:
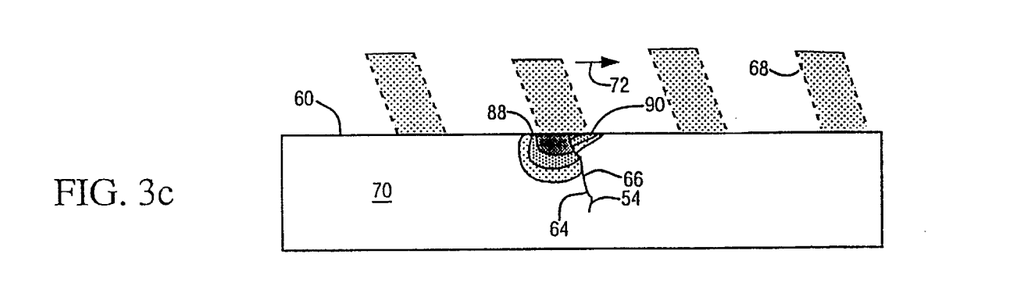

As shown in FIG. 3b, as a beam 68 and it's corresponding heated band 48 approach the crack 54, the crack 54 prevents preheating in front of the beam as would normally occur. Thus the small region 90 just on the other side of the crack 90 will remain cooler, longer, as the beam approaches it, because the crack 54 prevents the region 90 from being preheated. As illustrated in FIG. 3c, a beam 68 must substantially traverse the crack 54 before complete recovery of the preheat area 86, thus continuing the abnormally cool area 90 directly in front of the beam.

Figure 3D:
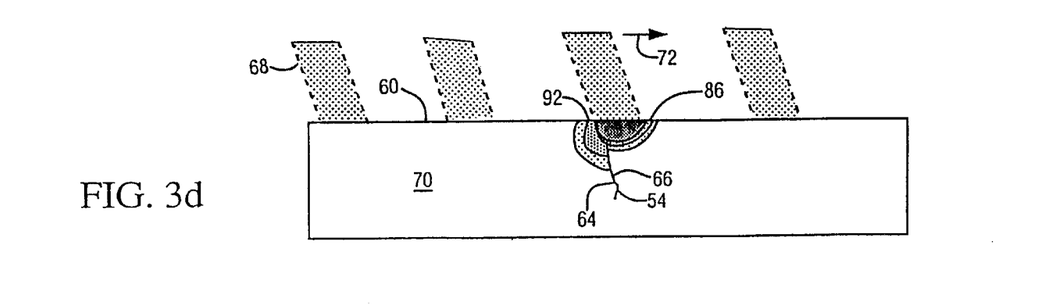
Figure 3E:
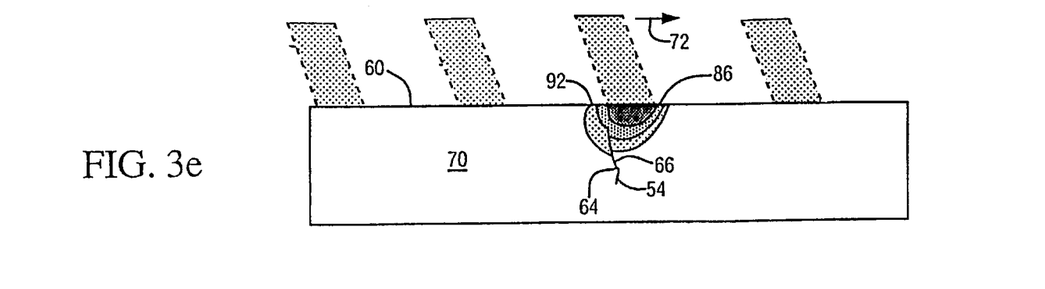

FIG. 3d illustrates how the insulating value of the crack 54, which causes a heat buildup on the upstream side 64 of the crack 54 as shown in FIGS. 3c and 3d, results in an extension of the lagging postheat zone 88, shown in FIG. 3c, which forms a hot spot 92 just upstream of the crack 54. This hot spot continues to be visible in FIG. 3e even after a beam has passed the crack, the additional heat built up on the upstream side continues to dissipate.

It is the small regions 90 of unusual coolness and the small regions of unusual high temperature 92 which are produced as the band 48 traverses the crack, which are brought out by the image processing spacial filter 56 and used to image thermal discontinuities within the test specimen 30, 60.

As shown in FIG. 1, an image 94 of a test object 30 is formed on a monitor 28. The test object is illustrated as an airplane 30. The image 94 shows portions of the airplane 30, including a lateral rivet seam 96, a vertical lap joint 98, and a window 100, as well as individual rivets 102. The structural features 96, 98, 100, and 102 of the test specimen would normally be visible as an output of the fast imaging processor 26, inasmuch as they represent changes in the thermal diffusivity of the test object 30. Thermal diffusivity is proportional to the thermal conductivity of a material divided by the product of the specific heat and material density. It represents the rate at which heat will propagate through a material. The presence of changes in material section, bond lines, lap lines, and rivet holes can all represent decreased thermal conductivity or a change in material which will affect the specific heat, and will thus produce temperature profile changes which may be imaged.

The image 94 also shows stress cracks 104 which produce thermal discontinuities. One advantage of the forced diffusion thermography apparatus 20 is that it can produce an image of the test object with recognizable features, allowing ready correlation between the observed defects and the actual test object.

Figure 8:
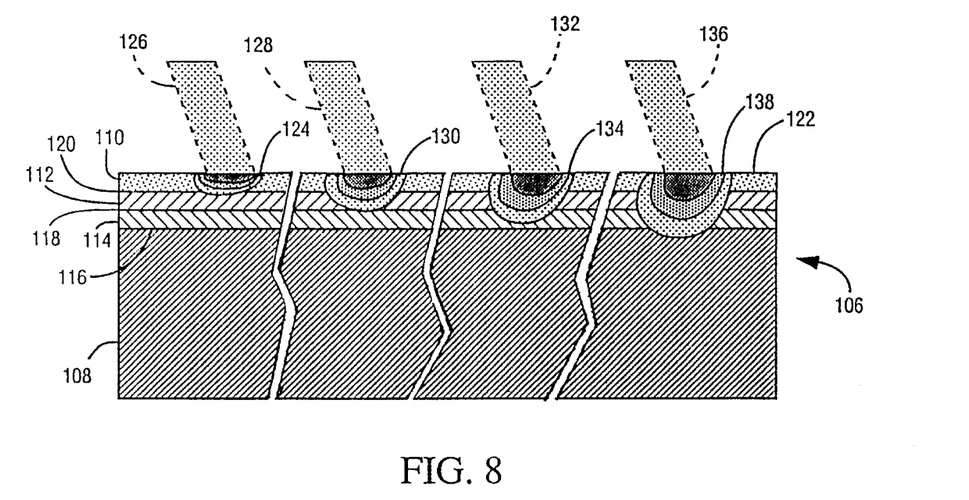
FIG. 8 is a broken cross-sectional view of a material having multiple surface coatings each broken portion of the material illustrating the heating caused by bars which are progressively moving at a lower velocity along the material.

A material cross-section 106 is shown in FIG. 8 and is representative of a portion of a complicated structure such as a turbine blade, which may consist of a substrate 108 overlain by three coating layers, a top coat 110, a mid-coat 112, and a bottom coat 114. Such constructions may be necessary in difficult engineering design environments, such as that experienced by a turbine blade in the hot section of a jet engine. The efficiency of a jet engine is limited by the maximum temperature which can be withstood by the turbine blades. The turbine blades are also highly stressed and may be subject to a hot oxidizing environment. No one material can meet all the design requirements of high strength, temperature resistance, and resistance to oxidation.

Thus, for illustrative purposes only, the substrate 108 might consist of a single crystal of metallic super alloy, upon which is deposited the bottom coat 114 which, for example, might be a coating which forms a tight bond along a bond-line seam 116 of the substrate. The mid-coat 112 might be an insulative layer joined by a mid-bond line 118 which in turn is overlain by an oxidation-resistant top layer 110, which is joined to the insulative layer by a top-bond line 120.

FIG. 8 illustrates the way in which projected bands of infrared heating which move at different speeds over the surface 122 of the material cross-section 106 produce heating which penetrates the varying depths within the material 106.

The first heating profile 124 illustrated in FIG. 8 represents the profile of heating produced by a projected infrared band 126 moving at a first rate. The heating occurs only in the top coating 110. The probe beam 126 which produces the heating profile 124 will only detect flaws within the top coat 110.

The second probe beam 128 moves at a second, reduced rate and creates a second profile 130, which penetrates into the second layer 112. Thus the heat profile appearance when viewed from the surface 122 will depend on the integrity or thermal conductivity of the top-bond line 120.

The third probe beam 132 travels at a third, still further reduced rate and produces a third heating profile 134 which penetrates into the bottom coating 114. Thus the heat profile 134 when viewed from the surface 122 will in part depend on the characteristics of the mid-bond line 118 and the internal characteristics of the mid-coat 112 and bottom-coat 114.

The fourth beam 136 of infrared radiation is traversing the surface 122 of the sample 106 sufficiently slowly that the heating profile 138 extends all the way to the substrate 108. Thus the heating profile 138 when viewed from the surface 122 will in part depend on the integrity of the bottom bond-line 116.

Of course, the heating profile 138 produced by the infrared beam 136 will be affected by all three coatings, 110, 112, and 114. However, because probe beams 126, 128, 132, 136 with different temporal frequencies or rates of travel over the surface 122 are employed, the information from the high frequency probe beams may be used in combination with the information from the lower frequency probe beams to distinguish features which are unique to the low velocity probe beams, and thus indicate flaws at greater depths within the center 106.

A simple relationship exists between the time it takes heat to reach a given depth and the thermal diffusivity. It is as follows. The time required for heating to move from the surface to a given depth is equal to $0.36\ L^2/\alpha$ where L is the layer thickness and $\alpha$ is the thermal diffusivity. Thus, the apparatus 20 can be used to measure the thickness of deposited layers if the thermal diffusivity of the material of which the layers is comprised is known. Likewise, the diffusivity of the material can be determined by standardized samples of known thickness for which the thickness is determined by another means, such as ultrasonic probe.

In FIG. 1, the IR projector 22 is shown as a simple mechanical light shield 32 for projecting simple bands 40 onto a test object 30. The frequency with which the bands 40 traverse the object 30 can be varied by varying the speed of rotation of the light shield 32. However, for many applications the ability to generate the patterns of arbitrary complexity will be desired. A simple example is that the apparatus 20 cannot detect cracks which are perpendicular to the direction of motion of the heating bands 40 because little or no heat is flowing along the length of the band. Therefore, it would be desirable to adjust the orientation of the bands to assure the detection of flaws in every direction.

A block diagram of a forced diffusion thermography apparatus and method is shown in FIG. 4. First, a pattern selection Step 140 is performed either by machine algorithm or by manual selection. The pattern selection involves both the frequency or orientation and the shape of the thermal pattern to be projected on the structure. Its selection is dependent on the type of flaw which is desirable to detect as well as the materials of which the specimen is comprised. The pattern generator 142 then creates or selects a pattern according to the pattern selection criteria. An IR projector 144 which utilizes a liquid crystal shutter interposed between an infrared source and infrared projecting optics may allow for projection of an arbitrary pattern. The liquid crystal shutter may consist of an array similar to that used for a computer display terminal and thus can use the output of a computer graphics program to form patterns of arbitrary complexity. Two exemplary complex patterns are illustrated in FIGS. 9 and 10.

Figure 9:
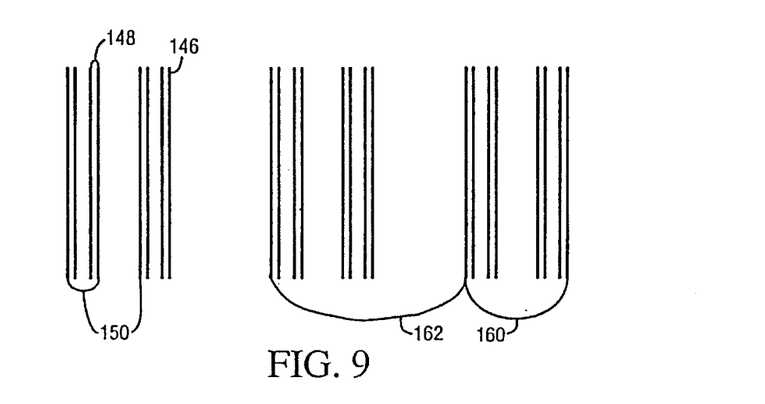
FIG. 9 is a test pattern for simultaneously analyzing the surface coatings of FIG. 8.
Figure 10:
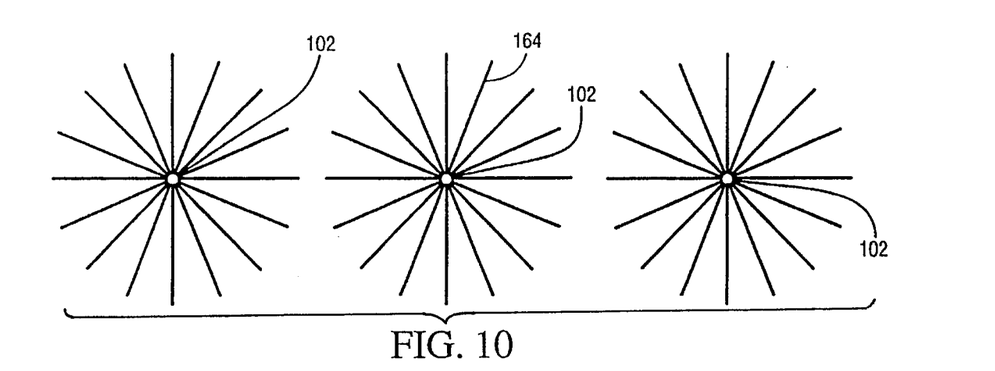
FIG. 10 is a test pattern optimized for detecting radial cracks about rivets.

FIG. 9 is illustrative of a pattern which might be used to probe varying depths of a material 106 such as shown in FIG. 8. Here, spatially positioning individual projected bands 146 which are grouped together provides different spatial frequencies. In FIG. 9, five separate spatial groupings are shown, starting with the individual bands 146, going to groups of bands 148, then groups of groups 150, which are combined to form higher order groups 160, which are combined in yet higher order groups 162.

The individual bands 146 have a spacing which when combined with the rate of movement across a material 106 produces a particular frequency which may be used to perform a lock-in amplification of the material response. The fact that them are gaps in the spacing of the bands 146 does not prevent the use of the frequency characteristic of the bands 146.

The existence of higher order groupings 148, 150, 160, and 162 can be used to perform lock-in amplification at the lower frequencies characteristic of the higher order groupings 148, 150, 160, and 163. This will have the effect of using the average heat input of the individual bands over the time dictated by the grouping of bands to produce bands of effective greater width though with lower amplitude.

An alternative method for probing the substance of FIG. 8 in depth would be to use bands of varying thickness. Bands of varying thickness, or groups of bands, as shown in FIG. 9, could be fabricated on a simple rotatable mask or light shield 32, such as shown in FIG. 1. On the other hand, using a general purpose infrared projector 144 as shown in FIG. 4, groups of bands moving at different velocities which therefore cross over each other during their traverse of a sample 30, 60, 106 could be used. Conceptually, patterns of high complexity may prove most advantageous. For instance, to detect cracks and in-depth delaminations, a sample might be illuminated either sequentially or simultaneously with three sets of projected infrared bands, each oriented at 60° to each other. Three sets of bands at 60° to each other should detect cracks at all orientations. Each set of bands may be sequenced in time or spatially to also probe the material in depth.

FIG. 10 illustrates how different patterns may be used sequentially to optimally analyze a structure. The airplane 30 in FIG. 1 is examined with a simple pattern to detect the thermal discontinuities caused by rivets. The computer image 94 is analyzed automatically or manually to detect rivets 102. A test pattern is generated and projected onto the test specimen airplane. The pattern, as shown in FIG. 10, has radial lines rotating about each rivet. This optimally detects stress cracks 104, which will tend to grow radially out from the rivets, which are optimally detected by a heating band 164, which is nearly parallel to the crack 104. Thus, in the optimal configuration of the forced diffusion thermography apparatus 20 illustrated in FIG. 4, the pattern selection Step or apparatus 140 will be interactive with the operator or with the output of the synchronized IR camera 166 in FIG. 5.

Although the use of an infrared projector 22, 144 is shown and described, it should be understood that a sufficiently high-power laser which is raster scanned, or scanned under computer control, could produce an output which would function similarly to the output of an infrared projector with a liquid crystal shutter. It should also be understood that a laser could be used as the source of illumination for the infrared projector with optics simply expanding the laser beam with sufficient width to illuminate the entire shutter.

Figure 2:
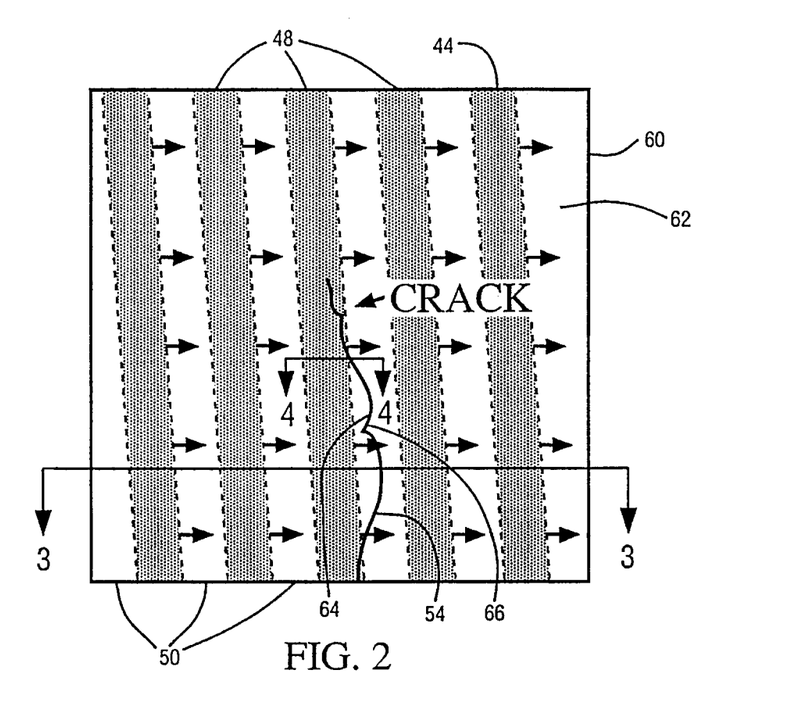
FIG. 2 is an illustrative plan view of the pattern of moving heating bands on an aluminum plate containing a crack.

For the purposes of demonstrating the forced diffusion thermography apparatus 20, a simple projection system in which a physical line pattern was configured to continuously travel in the screen plane of a 600 watt projector was used. The optical material used was such that no light with wavelengths exceeding 3 micrometers was transmitted. The detector used was sensitive to IR radiation wavelengths of up to 11.6 micrometers. A 6 micrometer IR high-pass filter was employed to eliminate direct reflective signals from the projector. Because of the low efficiency of the projector, less than 10 watts per square centimeter illuminated the specimen surface 62, as shown in FIG. 2. The specimen in FIG. 2 has a fatigue crack 54 which is grown in a 2.0 thick aluminum plate 60. The plate 60 was scanned with the forced diffusion thermography apparatus 20 with no load applied to the plate. The output of the synchronized camera is shown in thermal image 46 of FIG. 5, which after fast image processing resulted in the flaw image 58 of FIG. 5.

It should be understood that wherein the thermal pattern projector and infrared camera are shown as separate components of the apparatus 20 they could be combined into one instrument. Thus the optical paths leading from the projector, and to the infrared diode array could share a common optical train. The path would includes a spectral separating mirror or a switching mirror or shutter which would serve to separate the projected light from the received light. In addition to making a more compact instrument this would allow the use of a common focusing arrangement, which in turn would allow the infrared image on the diode array to be focused by focusing the projected pattern on the test object. Because of the sensitivity of the diode array to focus errors such an arrangement may significantly decrease the time and effort needed to set up and focus the forced diffusion thermography apparatus 20.

It should be understood that wherein an infrared filter is described for preventing the light of the projected pattern from being seen by the infrared camera, alternatively the light of the projected pattern could be chopped by being projected through a high frequency shutter interposed between the projector and the test object. The camera would be configured to view the test object only when the projector chopper shutter is closed. Another approach is to polarize the light of the projected pattern and view the test object through a cross polarized filter.

Figure 5:
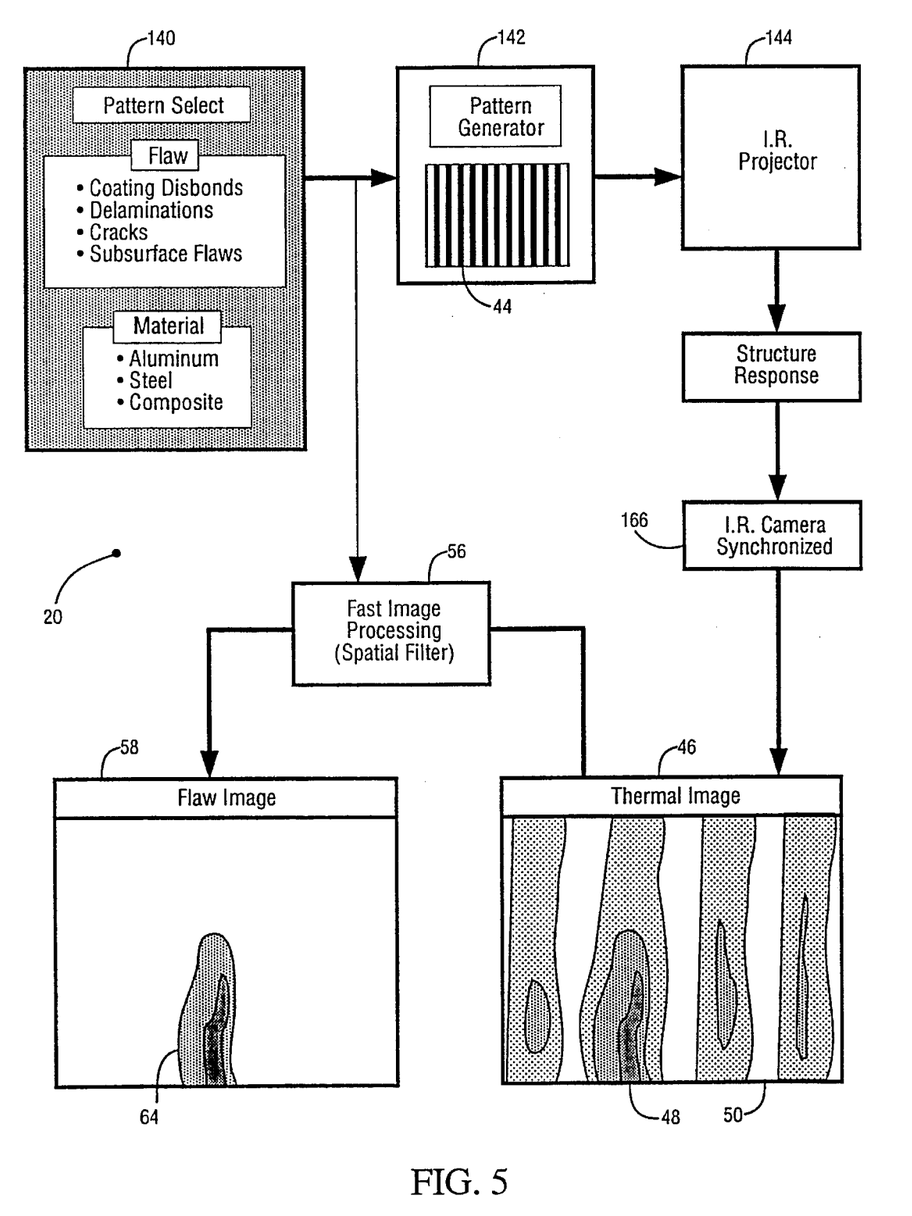
FIG. 5 is a schematic view of the process of this invention.

It should be understood that various types of image processing may be performed on the output of the synchronized IR camera 166 of FIG. 5. For example, the technique described by Favro, et al., *Inversion of Pulse Thermal-Wave Images for Defect Sizing and Shape Recovery*, 178/SPIE Vol 1682, Thermosense XIV, Universal Copyright Reporting System No. 0-8194-0843-3/92/$4. The technique disclosed in the foregoing paper could be used to sharpen the image of in-depth flaws produced by the synchronized IR camera 166 of the forced diffusion thermography apparatus 20.

It should also be understood that while the infrared pattern 44 will normally be projected onto the same surface as viewed by the infrared camera 24, in certain applications it may be desirable or possible to project the infrared band onto a surface of the test object which is hidden from direct view of the IR camera 24.

It should also be noted that wherein linear bands are optimal for detecting cracks, other patterns of infrared light, containing a multiplicity of spatial frequencies oscillating at a multiplicity of frequencies and phases, may be used. These could include but are not limited to geometric outlines, such as circles squares, triangles, etc., curved or curvilinear lines, as well as solid geometric shapes.

It should also be understood that the present invention is characterized over the prior art in that the infrared imaging system images a dynamic, moving pattern of infrared stimulation on the test object. This is as opposed to the flash lamp type system, where the entire surface of the object is illuminated by a high-power flash and the heat flows subsequent to the flash are monitored.

It should also be understood that the current system is distinguished from the prior art wherein a moving spot or line is projected on a sample, and where thermal heat flows are monitored by sensing the temperature off-set from the stimulation, the present invention achieves advantages by monitoring the entire field of view. Thus, the apparatus monitors the material directly beneath the heating beam as well as at all off-sets therefrom. This monitoring of an entire area which is being probed with a pattern of infrared heating results in the ability to differentiate surface and in-depth flaws.

It should also be understood that the present invention has advantages which distinguish over the prior art in that the moving pattern of projected thermal radiation provides the periodicity which allows correlation between the projected infrared pattern and the thermal response due to that pattern in a test object.

It should be noted that this invention provides a method for analyzing the structure of an article comprising the steps of illuminating an article to be tested with a moving pattern of radiation, viewing the article being tested with an infrared camera having a sensitivity to thermal radiation which is substantially outside the range of thermal radiation of the moving pattern; generating an output signal from the camera which corresponds to the varying temperature of the article; and processing the output signal of the camera to perform an auto-correlation in the time-domain to find the time-varying component of the thermal signal.

An additional method for analyzing the structure of a multi-layer article comprises the steps of illuminating an article to be tested with a first moving pattern of thermal radiation with a first time constant; illuminating the article to be tested with a second moving pattern of thermal radiation with a second time constant; viewing the article being tested with an infrared camera having a sensitivity to thermal radiation which is substantially outside the range of thermal radiation of the moving patterns; and processing the output signal of the camera to perform an auto-correlation in the time-domain to find the time-varying component of the thermal signal corresponding to at least the first and second moving patterns, wherein the first and second moving patterns create thermal patterns in the multi-layer article which penetrate to varying depths in the article, thus allowing the analysis of more than one layer.

A further method of this invention for analyzing the structure of a multi-layer article comprises the steps of illuminating an article to be tested with an arbitrary moving pattern of thermal radiation, the pattern having at least two different components with different time constants; detecting the thermal radiation emitted from the article being tested with an infrared camera having a sensitivity to thermal radiation which is substantially outside the range of thermal radiation of the moving pattern, and generating an output signal which corresponds to the detected radiation; and processing the output signal of the camera to perform an auto-correlation in the time domain to find at least the time-varying component of the thermal signal corresponding to the arbitrary moving pattern, wherein the at least two pattern components create thermal patterns in the multi-layer article that penetrate to varying depths in the article, thus allowing for the analysis of more than one layer.

Yet another method of this invention for analyzing a structure, for example for detecting radial cracks in an article having at least one possible site for radial crack development, comprises the steps of illuminating an article to be tested with a pattern of thermal radiation; detecting the thermal radiation emitted by the article being tested and generating an output signal corresponding thereto; processing the output signal to locate possible sites of radial crack development; illuminating the article to be tested with a radially rotating pattern of thermal radiation, wherein the pattern of thermal radiation rotates about the located possible sites of radial crack development; detecting the thermal radiation emitted by the illuminated article and generating an output signal corresponding thereto; and processing the output signal of the camera to perform an auto-correlation in the time domain to find the time-varying component of the thermal signal.

It is understood that the invention has advantages over the prior art which are not confined to those set forth but includes such advantages as are distinguished by the limitations of the following claims.

It is also understood that the invention is not confined to the particular construction and arrangement of parts herein illustrated and described, but embraces such modified forms thereof as come within the scope of the following claims.

I claim:

1. A method for analyzing the structure of an article comprising the steps of:
   (a) illuminating an article to be tested with a moving pattern of thermal radiation;
   (b) viewing the article being tested with an infrared camera having a sensitivity to thermal radiation which is substantially outside the range of thermal radiation of the moving pattern;
   (c) generating an output thermal signal from the camera which corresponds to the varying temperature of the article due to said moving pattern of thermal radiation;

(d) processing the output signal of the camera to perform an auto-correlation in the time-domain to find the time-varying component of the output thermal signal; and (e) analyzing said time-varying component to determine the structure of the article.

2. The method of claim 1 wherein the moving pattern of thermal radiation comprises a first moving pattern of thermal radiation with a first time constant and a second moving pattern of thermal radiation with a second time constant; and the step of processing the output signal to perform an auto-correlation in the time domain comprises processing the output signal of the camera to perform an auto-correlation in the time-domain to find the time-varying component of the thermal signal corresponding to at least the first and second moving patterns, wherein the first and second moving patterns create thermal patterns which penetrate to varying depths in the article.

3. The method of claim 1 wherein the moving pattern of radiation with which the article is illuminated comprises an arbitrary moving pattern of thermal radiation having at least two different components with different time constants; and wherein the processing step comprises processing the output signal of the camera to perform an auto-correlation in the time domain to find at least the time-varying component of the thermal signal corresponding to the arbitrary moving pattern, wherein the at least two pattern components create thermal patterns that penetrate to varying depths in the article.

4. The method of claim 1 wherein the moving pattern of radiation with which the article is radially rotating, and wherein the moving pattern of thermal radiation rotates about located possible sites of radial crack development.

* * * * *